(12) United States Patent
Hester, Jr.

(10) Patent No.: US 6,281,210 B1
(45) Date of Patent: Aug. 28, 2001

(54) BENZOIC ACID ESTERS OF OXAZOLIDINONES HAVING A HYDROXYACETYLPIPERAZINE SUBSTITUENT

(75) Inventor: Jackson B. Hester, Jr., Galesburg, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/732,088

(22) Filed: Dec. 6, 2000

Related U.S. Application Data

(60) Provisional application No. 60/170,675, filed on Dec. 14, 1999.

(51) Int. Cl.$^7$ ............... C07D 413/10; A61K 31/495; A61P 31/04
(52) U.S. Cl. ............... 514/235.8; 514/255.01; 544/367; 544/369; 544/374; 544/121
(58) Field of Search ............... 514/255.01, 235.8; 544/367, 369, 374, 121

(56) References Cited

U.S. PATENT DOCUMENTS 5,652,238 * 7/1997 Brickner et al. ............... 514/235.8

FOREIGN PATENT DOCUMENTS

WO 98/54161 * 12/1998 (WO).

* cited by examiner

*Primary Examiner*—Deborah C. Lambkin
*Assistant Examiner*—Andrea M. D'Souza
(74) *Attorney, Agent, or Firm*—Lucy X. Yang

(57) ABSTRACT

The present invention provides a compound of formula I

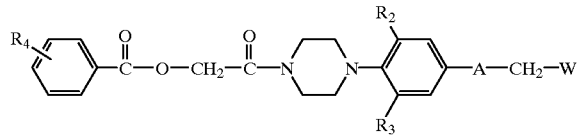

which have potent activities against gram positive and gram-negative bacteria.

24 Claims, No Drawings

BENZOIC ACID ESTERS OF OXAZOLIDINONES HAVING A HYDROXYACETYLPIPERAZINE SUBSTITUENT

CROSS REFERENCE

This application claims the benefit of the following provisional application: U.S. Ser. No: 60/170,675, filed Dec. 14, 1999, under 35 USC 119(e)(i).

FIELD OF THE INVENTION

The present invention relates to novel benzoic acid esters of oxazolidinones having a hydroxyacetylpiperazine substituent and their preparations. These compounds have potent activities against gram positive and gram-negative bacteria.

BACKGROUND OF THE INVENTION

The oxazolidinone antibacterial agents are a novel synthetic class of antimicrobials with potent activity against a number of human and veterinary pathogens, including gram-positive aerobic bacteria such as multiply-resistant staphylococci and streptococci, anaerobic organisms such as bacteroides and clostridia species, and acid-fast organisms such as *Mycobacterium tuberculosis* and *Mycobacterium avium*.

However, oxazolidinones generally do not demonstrate an activity at a useful level against aerobic gram-negative organisms. Thus, the use of these oxazolidinone antibacterial agents is limited to infectious states due to gram-positive bacteria. Accordingly, it is among the objects of the present invention to provide pharmaceutical compounds, which have broader antibacterial activity including the activity against aerobic gram-negative organisms. We have now discovered that the oxazolidinones of the present invention increase the spectrum of activity to include gram-negative organisms such as *Haemophilus influenza* and *Moraxella catarrhalis*. In addition, the compounds of the present invention are excellent water soluble agents, which makes them particularly useful for IV and oral administration for the treatment of microbial infections.

INFORMATION DISCLOSURE

U.S. Pat. No. 5,652,238 discloses carboxylic and phosphate esters of substituted-hydroxyacetyl piperazine phenyl oxazolidinones.

PCT International Publication WO 98/54161 discloses oxazolidinone antibacterial agents having a thiocarbonyl functionality.

SUMMARY OF THE INVENTION

The present invention provides a compound of formula I

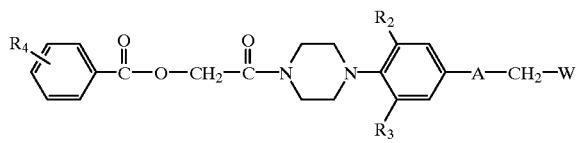

I or a pharmaceutically acceptable salt thereof wherein:

A is a structure i, ii, iii, or iv

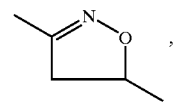

i

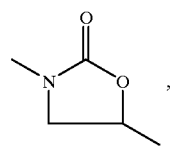

ii

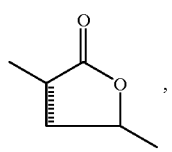

iii

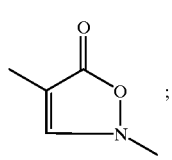

iv

W is
  a) NHC(=X)$R_1$,
  b) —O—het, —S—het, or —NH—het; provided that when A is a structure iv, W is not the section b);
X is O, or S;
$R_1$ is
  (a) H,
  (b) $NH_2$,
  (c) $NHC_{1-4}$alkyl,
  (d) $C_{1-4}$alkyl, optionally substituted by one or more F, Cl, or CN,
  (e) $C_{2-4}$alkenyl,
  (f) $OC_{1-4}$alkyl,
  (g) $SC_{1-4}$alkyl, or
  (h) $(CH_2)_n C_{3-6}$cycloalkyl;
$R_2$ and $R_3$ are independently H, F, Cl or $C_{1-2}$alkyl;
$R_4$ is positioned at either C-3 or C-4 and is:

(a)

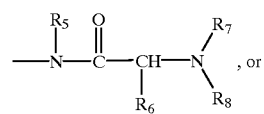, or (b)

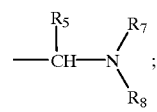;

$R_5$ is H, or $CH_3$;
$R_6$ is H, or $C_{1-4}$alkyl, optionally substituted by OH, SH, $SCH_3$, $NH_2$ or NHC(=NH)$NH_2$;
$R_7$ and $R_8$ are independently H, $C_{1-4}$alkyl, or $R_7$ and $R_8$ together with the nitrogen to which they are attached to form a saturated 5-, 6-, or 7-membered heterocyclic ring which may have additional heteroatoms selected from the group consisting of O, S(O)$_n$, or N—R$_5$; het is a C-linked five- (5) or six- (6) membered saturated or unsaturated heterocyclic ring having 1, 2, or 3 heteroatoms selected from the group consisting of oxygen, sulfur, and nitrogen, which is optionally fused to a benzene ring; at each occurrence, het is optionally substituted with one or more halo, OH, CF$_3$, OC$_{1-6}$ alkyl, CN, C$_{1-6}$alkyl, S(=O)$_n$R$^9$, C(=X)R$^{10}$, OC(=O) R$^{10}$, NHC(=O)R$^{10}$, or NR$^{10}$R$^{10}$, oxo, or oxime; wherein R$^9$ is C$_{1-6}$alkyl, aryl, or NR$^7$R$^8$; R$^{10}$ is H, C$_{1-6}$alkyl, aryl, or NR$^7$R$^8$; n is 0, 1, or 2; and with the proviso that when X is O, R$_4$ is not the subsection (a).

In another aspect, the present invention also provides:

a pharmaceutical composition comprising a compound of formula I or a pharmaceutically acceptable salt thereof, and a pharmaceutically acceptable carrier, a method for treating gram-positive microbial infections in humans or other warm-blooded animals by administering to the subject in need a therapeutically effective amount of a compound of formula I or a pharmaceutically acceptable salt thereof, and a method for treating gram-negative microbial infections in humans or other warm-blooded animals by administering to the subject in need a therapeutically effective amount of a compound of formula I or a pharmaceutically acceptable salt thereof.

The invention also provides some novel intermediates and processes that are useful for preparing compounds of formula I.

DETAILED DESCRIPTION OF THE INVENTION

The following definitions are used, unless otherwise described.

The term alkyl, alkenyl, etc. refer to both straight and branched groups, but reference to an individual radical such as "propyl" embraces only the straight chain radical, a branched chain isomer such as "isopropyl" being specifically referred to.

The carbon atom content of various hydrocarbon-containing moieties is indicated by a prefix designating the minimum and maximum number of carbon atoms in the moiety, i.e., the prefix C$_{i-j}$ indicates a moiety of the integer "i" to the integer "j" carbon atoms, inclusive. Thus, for example, C$_{1-7}$ alkyl refers to alkyl of one to seven carbon atoms, inclusive.

Mammal refers to human or animals.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "O" for oxygen atom, "S" for sulfur atom, "N" for nitrogen atom, "h" for hour or hours and "rt" for room temperature).

The term "het" refers to a C-linked five- (5) or six- (6) membered heterocyclic ring having 1, 2, or 3 heteroatoms selected from the group consisting of oxygen, sulfur, and nitrogen, which is optionally fused to a benzene ring.

Examples of "het" include pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, or 1,2,4-dithiazolone.

At each occurrence, het may be substituted with one or more group as defined in the summary of the invention or in claims.

A specific value for het is isoxazol-3-yl, isoxazol-5-yl, 1,2,4-oxadiazol-3-yl, isothiazol-3-yl, 1,2,4-thiadiazol-3-yl or 1,2,5-thiadiazol-3-yl.

Specific and preferred values listed below for radicals, substituents, and ranges, are for illustration only; they do not exclude other defined values or other values within defined ranges for the radicals and substituents.

Specifically, C$_{1-4}$ alkyl, can be an alkyl group having one to four carbon atoms such as, for example, methyl, ethyl, propyl, butyl, and their isomeric forms thereof; C$_{2-4}$ alkenyl can be vinyl, propenyl, allyl, butenyl, and their isomeric forms thereof; C$_{3-6}$ cycloalkyl can cyclopropyl, cyclobutyl, cyclopentyl, cyclohexyl, and their isomeric forms thereof.

A specific value for A is structure ii as defined above.

A specific value for X is sulfur atom.

A specific value for X is oxygen atom.

A specific value for R$_1$ is C$_{1-4}$alkyl.

A more specific value for R$_1$ is ethyl.

A specific value for R$_1$ is cyclopropyl.

A specific value for R$_1$ is NH$_2$.

A specific value for R$_2$ and R$_3$ are independently H or F.

A specific value for R$_2$ and R$_3$ are that one of them is H, the other one is F.

A specific value for R$_4$ is —CH$_2$N(CH$_3$)$_2$.

A specific value for R$_4$ is 4-morpholinylmethyl.

A specific value for R$_4$ is 4-methyl-1-piperazinylmethyl.

A specific value is that R$_4$ is positioned at either C-3 or C-4. The positions C-3 and C-4 refer to the following positions respectfully:

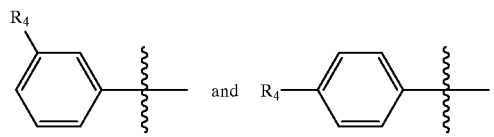

The preferred compounds of the present invention are those wherein structure i, ii, or iii has an optical configuration below:

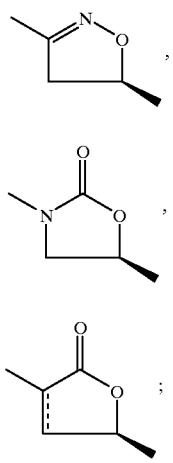

These absolute configurations are called (S)-configuration according to the Cahn-Ingold-Prelog nomenclature system.

Examples of the present invention are:

(1) (S)-N-[[3-[3-fluoro-4-[4-(hydroxyacetyl)-1-piperazinyl] phenyl]-2-oxo-5-oxazolidinyl]methyl]propanethioamide 4-[(dimethylamino)methyl]benzoic acid ester, (2) (S)-N-[[3-[3-fluoro-4-[4-[(hydroxy acetyl)-1-piperazinyl]phenyl]-2-oxo-5-oxazolidinyl]methyl] propanethioamide 3-[(dimethylamino)methyl]benzoic acid ester, (3) (S)-N-[[3-[3-fluoro-4-[4-[(hydroxyacetyl)-1-piperazinyl]phenyl]-2-oxo-5-oxazolidinyl]methyl] propanethioamide 3-(morpholinomethyl)benzoic acid ester, (4) (S)-N-[[3-[3-fluoro-4-[4-(hydroxyacetyl)-1-piperazinyl] phenyl]-2-oxo-5-oxazolidinyl]methyl]propanethioamide 3-[(4-methyl-1-piperazinyl)methyl]benzoic acid ester, (5) (S)-N-[[3-[3-fluoro-4-[4-(hydroxyacetyl)-1-piperazinyl] phenyl]-2-oxo-5-oxazolidinyl]methyl]propanethioamide 3-[(diethylamino)methyl]benzoic acid ester, (6) (S)-N-[[3-[3-fluoro-4-[4-(hydroxyacetyl)-1-piperazinyl] phenyl]-2-oxo-5-oxazolidinyl]methyl]propanethioamide 4-[(diethylamino)methyl]benzoic acid ester, (7) (S)-N-[[3-[3-fluoro-4-[4-(hydroxyacetyl)-1-piperazinyl] phenyl]-2-oxo-5-oxazolidinyl]methyl]propanethioamide 4-(morpholinomethyl)benzoic acid ester, (8) (S)-N-[[3-[3-fluoro-4-[4-(hydroxyacetyl)-1-piperazinyl] phenyl]-2-oxo-5-oxazolidinyl]methyl]propanethioamide 4-[(4-methyl-1-piperazinyl)methyl]benzoic acid ester, (9) (S)-N-[[3-[3-fluoro-4-[4-(hydroxyacetyl)-1-piperazinyl] phenyl]-2-oxo-5-oxazolidinyl]methyl] cyclopropanecarbothioamide 4-[(dimethylamino)methyl] benzoic acid ester,

(10) (S)-N-[[3-[3-fluoro-4-[4-(hydroxyacetyl)-1-piperazinyl]phenyl]-2-oxo-5-oxazolidinyl]methyl] thiourea 4-[(dimethylamino)methyl]benzoic acid ester,

(11) (S)-N-[[3-[3-fluoro-4-[4-(hydroxyacetyl)-1-piperazinyl]phenyl]-2-oxo-5-oxazolidinyl]methyl] propanethioamide 4-(glycylamino)benzoic acid ester,

(12) (S)-N-[[3-[3-fluoro-4-[4-(hydroxyacetyl)-1-piperazinyl]phenyl]-2-oxo-5-oxazolidinyl]methyl] cyclopropanecarbothioamide 4-(glycylamino)benzoic acid ester, or

(13) (S)-N-[[3-[3-Fluoro-4-[4-(hydroxyacetyl)-1-piperazinyl]phenyl]-2-oxo-5-oxazolidinyl]methyl] propanethioamide 4-(L-alanylamino)benzoic acid ester.

The following Schemes describe the preparation of compounds of the present invention. All of the starting materials are prepared by procedures described in these schemes or by procedures that would be well known to one of ordinary skill in organic chemistry. The variables used in the Schemes are as defined below or as in the claims. The compounds of this invention can be prepared in accordance to one or more of the Schemes discussed below.

As shown in Scheme I, compound 1-a with an appropriate amino protecting group (P) is esterified with either 3- or 4-nitrobenzoyl chloride to provide compound 1-b. In this reaction a tertiary amine base such as triethylamine may be used to neutralize the hydrogen chloride formed. Non-protic solvents such as $CH_2Cl_2$ or THF and temperatures in the range of 0–24° C. are suitable for this reaction. Protecting groups (P) are chosen for their compatibility with the chemistry and functional groups of the molecules being synthesized. For the compounds synthesized in Examples 1–12 tert-butoxycarbonyl (Boc) is a suitable protecting group; however, depending on the chemistry and compounds desired other protecting groups may be employed. Synthesis of Compound 1-b wherein P is Boc is described in PCT International Publication WO 98/54161 and exemplified in Example 1 of the present invention. The nitro group of Compound 1-b is reduced to the amine to provide compound 1-c. This is conveniently accomplished by catalytic hydrogenation with a palladium catalyst in solvents such as MeOH, EtOH and $CH_2Cl_2$ at room temperature; however, other catalytic or chemical methods known to one skilled in the art can be employed if desired. Compound 1-c where $R_5$ is methyl can be obtained by alkylating the amine formed in this reaction. Acylating the aniline 1-c with an appropriately activated amino acid derivative provides 1-d. Example 11, Step 3 illustrates the use of an acid chloride and tertiary amine base for this reaction; however, condensing agents such as 1,1'-carbonyldiimidazole and 1,3-dicyclohexylcarbodiimide/1-hydroxybenzotriazole which are well known in the art of peptide chemistry can also be used for this reaction. In Schemes I, II and III when $R_6$ contains an OH or SH and when $R_7$ and or $R_8$ are hydrogen a protecting group (P') may be required. Example 11, Step 3 illustrates the use of 9-fluorenylmethoxycarbonyl (Fmoc) for protecting the amino group of glycine. Fmoc is stable to conditions suitable for removing Boc (Example 11, Step 4) but can be readily removed (piperidine in DMF) in the presence of a thioamide (Example 11, Step 6). The benzyloxycarbonyl can also be removed (HBr/HOAc) in the presence of a thioamide and is thus a suitable P' group. Compound 1-d is deprotected to provide 1-e. Acylating 1-e provides 1-f. Any additional protecting groups (P') can be then removed at this stage. Removal of the Boc protecting group from 1-d can be conveniently carried out with HCl in dioxane to give the hydrochloride salt of the amine. This salt can often be used directly in the subsequent acylation. Acylation of the amine or amine hydrochloride 1-e with dithioesters and a tertiary amine base to give thioamides is carried out in solvents such as $CH_2Cl_2$, THF or preferably MeOH at temperatures in the range of 24–50° C. Preparations of other thiocarbonyl compounds can be prepared according to the procedures described in PCT International Publication WO 98/54161.

In Scheme II the intermediate alcohol 2-a is esterified with a 3- or 4-(1-chloroalkyl)benzoyl chloride and a tertiary amine base in an appropriate solvent such as $CH_2Cl_2$ at a temperature in the range of 0–40° C. to give compound 2-b. Alkylation of an amine with 2-b provides compound 2-c. The reaction can be carried out in solvents such as acetone or $CH_2Cl_2$ with a catalytic amount of sodium iodide at a temperature ranging from ambient to the reflux temperature of the solvent. Deprotection of 2-c to provide 2-d, and the preparation of compounds 2-e are carried out by the same procedures described in Scheme I.

In Scheme II the alcohol intermediate 3-a is esterified with an appropriately substituted benzoic acid

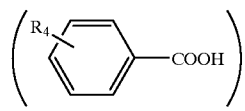

to provide compound 3-b. As described in Schemes I and II, the acid chlorides and a tertiary amine base can be used for this reaction. In addition this reaction can be carried out with reagent systems such as 1,3-dicyclohexylcarbodiimide and 4-dimethylaminopyridine or triphenylphosphine and diethyl azodicarboxylate. The remaining steps which lead to the compounds of formula I of the present invention are carried out by the same procedures described in Schemes I and II.

SCHEME I

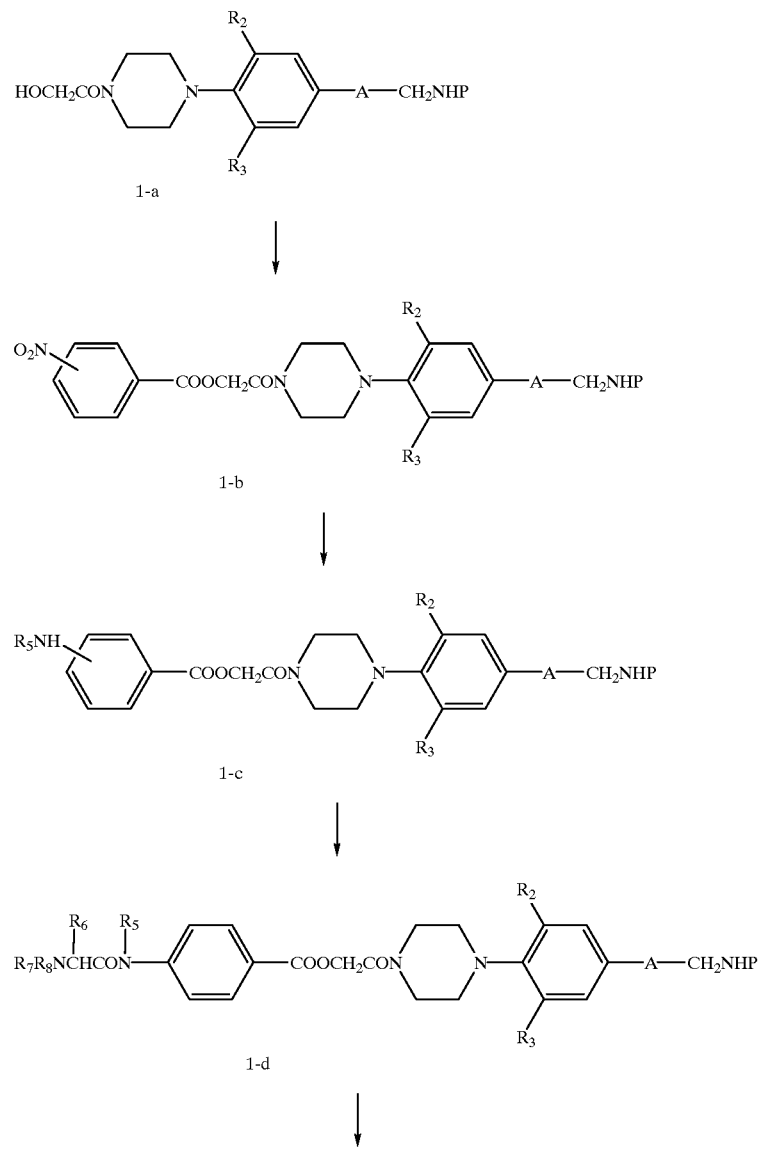

-continued
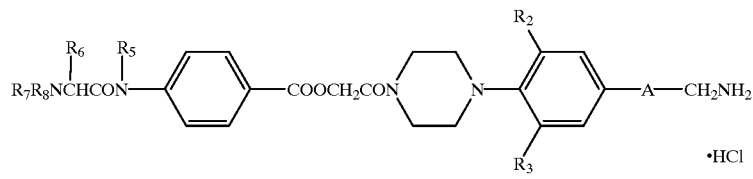
1-e
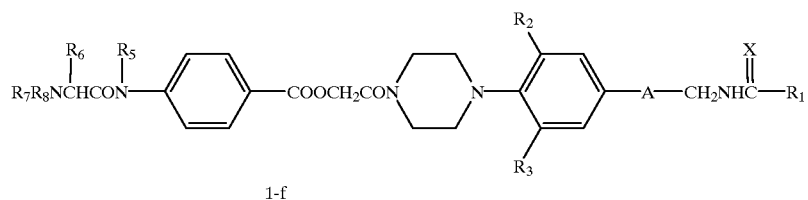
1-f
SCHEME II
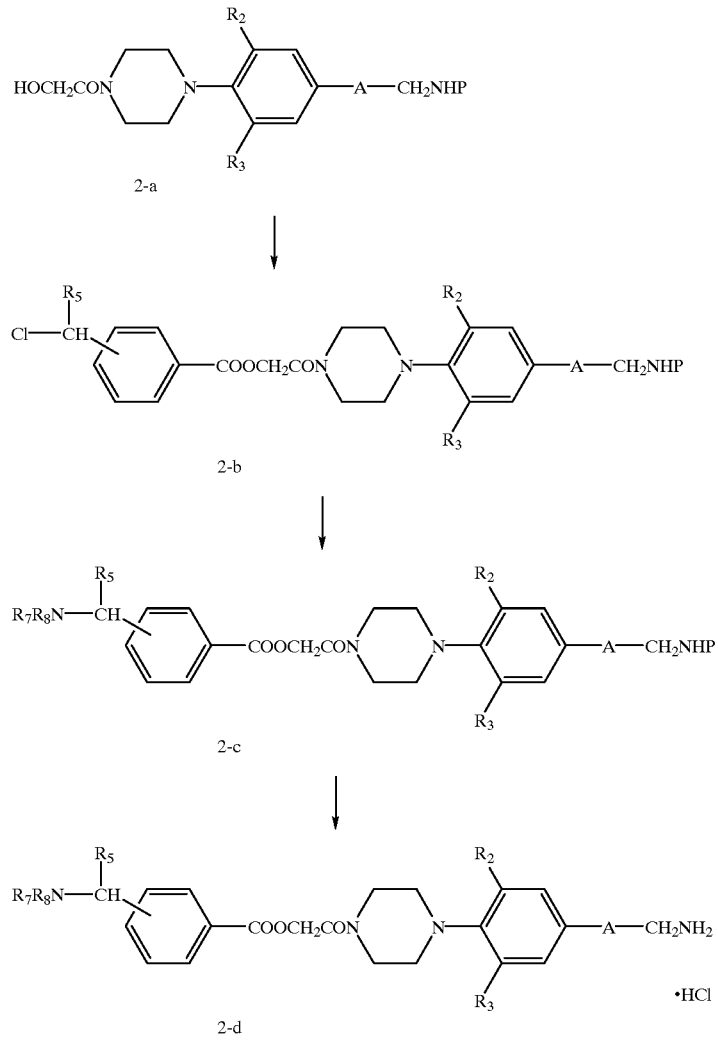

-continued

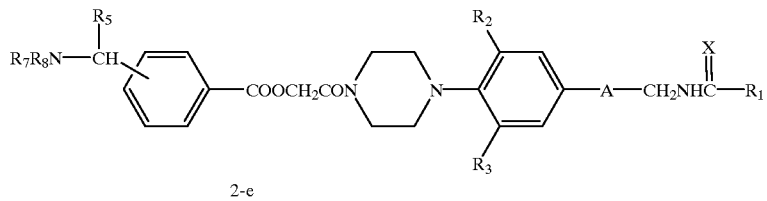

2-e

SCHEME III

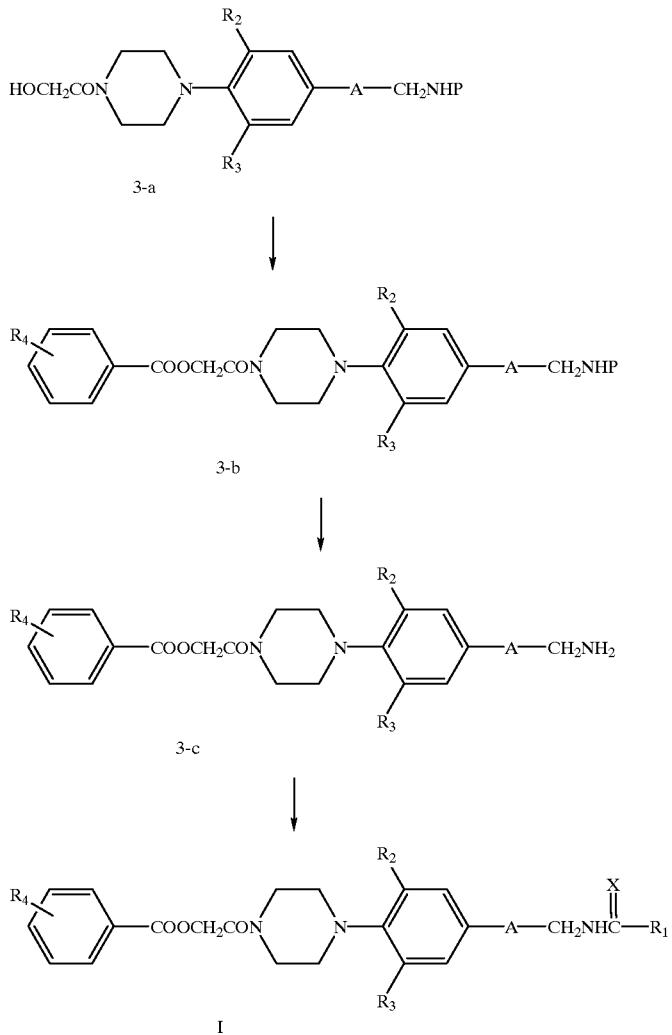

The pharmaceutical compositions of this invention may be prepared by combining the compounds of Formula I of this invention with a solid or liquid pharmaceutically acceptable carrier and, optionally, with pharmaceutically acceptable adjuvants and excipient employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compounds of formula I according to this invention.

The quantity of active component, that is the compound of formula I according to this invention, in the pharmaceutical composition and unit dosage form thereof may be varied or adjusted widely depending upon the particular application, the potency of the particular compound and the desired concentration. Generally, the quantity of active component will range between 0.5% to 90% by weight of the composition.

In therapeutic use for treating, or combating, bacterial infections in warm-blooded animals, the compounds or pharmaceutical compositions thereof will be administered orally, topically, transdermally, and/or parenterally at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 1.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of formula I according to this invention are administered parenterally, i.e., by injection, for example, by intravenous injection or by other parenteral routes of administration. Pharmaceutical compositions for parenteral administration will generally contain a pharmaceutically acceptable amount of the compound according to formula I as a soluble salt (acid addition salt or base salt) dissolved in a pharmaceutically acceptable liquid carrier such as, for example, water-for-injection and a buffer to provide a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine to name but a few representative buffering agents. The compounds according to formula I generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the above-mentioned antibacterially effective amount of dosage. The compounds of formula I according to this invention are advantageously administered orally in solid and liquid dosage forms.

The oxazolidinone antibacterial agents of this invention have useful activity against a variety of organisms. The in vitro activity of compounds of this invention can be assessed by standard testing procedures such as the determination of minimum inhibitory concentration (MIC) by agar dilution as described in "Approved Standard. Methods for Dilution Antimicrobial Susceptibility Tests for Bacteria That Grow Aerobically", 3rd. ed., published 1993 by the National Committee for Clinical Laboratory Standards, Villanova, Pa., USA. The activity of compounds of this invention against *Staphylococcus aureus, Staphylococcus epidermidis, Streptococcus pneumoniae, Enterococcus faecalis, Moraxella catarrhalis* and *H. influenzae* is shown in Table 1.

Antibacterial Activity Minimum Inhibitory Concentration (μg/mL)

TABLE 1

| Ex-number | SAUR. 9213 SAUR 9213 MIC | SEPI 30593 SEPI 30593 MIC | EFAE 12712 EFAE 12712 MIC | SPNE 9912 SPNE 9912 MIC | SPYO 152 SPYO 152 MIC | HINF 30063 HINF 30063 MIC | EFAE 9217 EFAE 9217 MIC | MCAT 30607 MCAT 30607 MIC |
|---|---|---|---|---|---|---|---|---|
| 1 | 0.5 | 0.25 | 0.5 | <0.06 | <0.06 | 4 | 0.25 | 0.5 |
| 2 | 1 | 0.25 | 0.5 | 0.125 | <0.06 | 8 | 0.5 | 0.5 |
| 3 | 4 | 2 | 2 | 0.5 | 0.5 | 64 | 2 | 4 |
| 4 | 8 | 2 | 2 | 0.5 | 0.5 | 64 | 2 | 4 |
| 5 | 2 | 2 | 2 | 0.25 | 0.25 | 32 | 1 | 2 |
| 6 | 2 | 1 | 1 | 0.25 | 0.125 | 16 | 1 | 2 |
| 7 | 2 | 2 | 2 | 0.5 | 0.25 | 64 | 1 | 4 |
| 8 | 2 | 1 | 1 | 0.125 | 0.125 | 16 | 1 | 1 |
| 9 | 0.5 | 0.125 | 0.5 | <0.06 | <0.06 | 8 | 0.5 | 0.5 |
| 10 | 4 | 0.5 | 0.5 | 0.125 | <0.06 | 8 | 0.5 | 2 |

EXAMPLES

Example 1

(S)-N-[[3-[3-Fluoro-4-[4-(hydroxyacetyl)-1-piperazinyl]phenyl]-2-oxo-5-oxazolidinyl]methyl] propanethioamide 4-[(dimethylamino)methyl] benzoic acid ester (7)

Step 1:

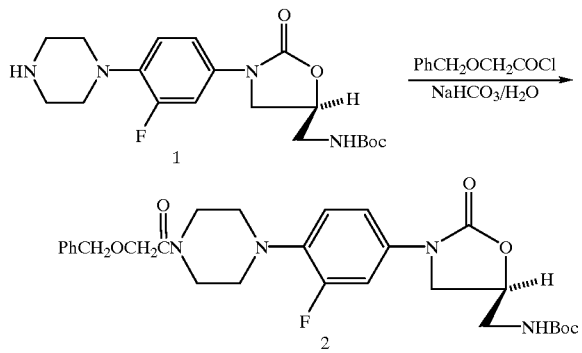

A stirred, ice cold mixture of 1 (PCT International Publication WO 98/54161) (20.0 g, 50.7 mmol), acetone (1500 mL) and saturated aqueous sodium bicarbonate (500 ml) is treated, during 20 min, with a solution of benzyloxyacetyl chloride (9.5 ml, 60.8 mmol) in acetone (150 ml). The mixture is allowed to warm slowly to ambient temperature (24° C.) and stand for 18 hours. It is extracted with Et$_2$O and the extract is washed with water and brine, dried (MgSO$_4$), and concentrated to give 25.4 g of the product 2.

Step 2:

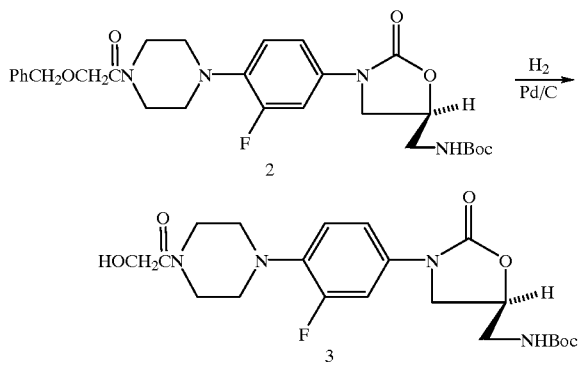

A mixture of 2 (25.0 g, 46.1 mmol), MeOH (1700 ml) and 10% palladium—on—carbon catalyst (6.25 g) is hydrogenated at an initial pressure of 35 p.s.i. for 4 days. Additional catalyst (6.25 g) is added and the hydrogenation is continued for 1 day. The mixture is filtered and the filtrate is concentrated. Chromatography of the residue on silica gel with 2.5% MeOH—CH$_2$Cl$_2$ gave the product which is crystallized from acetone—CH$_2$Cl$_2$ to give 13.7 g of 3.

Step 3:

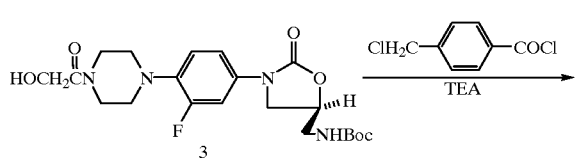

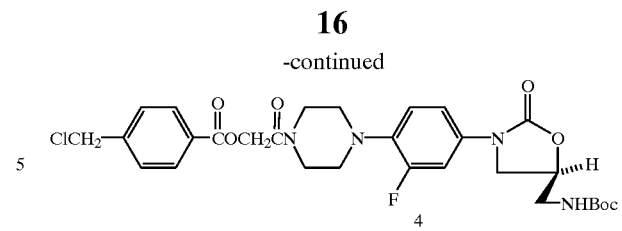

A stirred mixture of 3 (5.70 g, 12.6 mmol) and triethylamine (2.99 ml, 21.4 mmol) in CH$_2$Cl$_2$ (76 ml) is treated at ambient temperature (24° C.) with a solution of 4-(chloromethyl)benzoyl chloride (3.57 g, 18.9 mmol) in CH$_2$Cl$_2$ (32 ml) and kept at ambient temperatures for 4 days. It is washed with saturated aqueous NaHCO$_3$, dried (MgSO$_4$) and concentrated. Chromatography of the residue on silica gel with 5% MeOH/CH$_2$Cl$_2$ gave the product which is dissolved in CH$_2$Cl$_2$ (40 ml) and precipitated with hexane to give 5.37 g of 4.

Step 4:

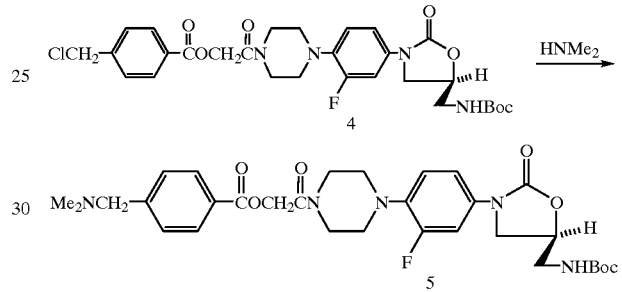

A stirred mixture of 4 (650 mg, 1.05 mmol), NaI (11 mg), 2M dimethylamine in MeOH (2.1 ml, 4.20 mmol) and acetone (14 ml) is kept at ambient temperature for 24 h, mixed with water (20 ml) and extracted with CH$_2$Cl$_2$. The extracts are dried (MgSO$_4$) and concentrated. Chromatography of the residue on silica gel with 5% MeOH/0.5% NH$_4$OH/CH$_2$Cl$_2$ gave 559 mg of 5.

Step 5:

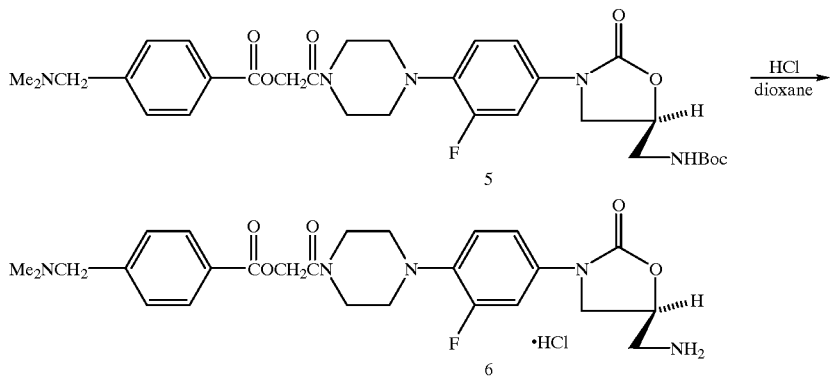

Compound 5 (520 mg, 0.847 mmol) is cooled in an ice bath and treated with 4N HCl in dioxane (10 ml). The mixture is stirred in the ice bath for 2 hours and at ambient temperature (24° C.) for 1.5 hours and concentrated. Three 4.0 ml portions of CH$_2$Cl$_2$ are mixed with the residue with concentration after each addition to give 6.

Step 6:

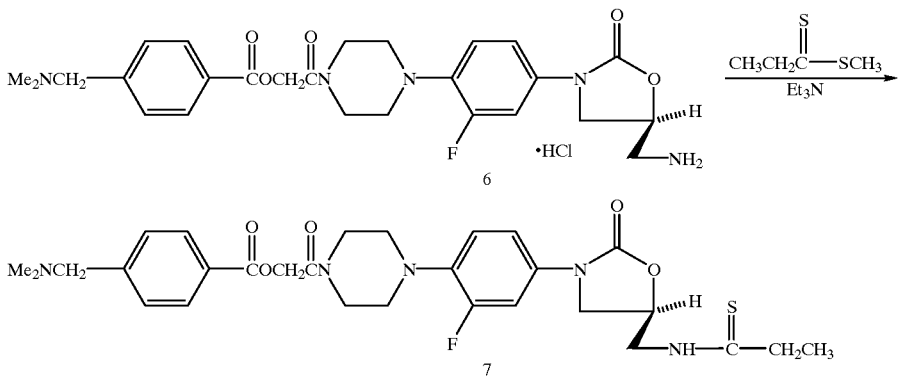

A stirred mixture of 6 (400 mg, 0.727 mmol), triethylamine (0.81 ml, 5.82 mmol) and methyl dithiopropionate (350 mg, 2.91 mmol) in CH$_2$Cl$_2$ (7 ml)/THF (7 ml) is kept at ambient temperature (24° C.) for 2 days, mixed with water and extracted with CH$_2$Cl$_2$. The extract is dried (MgSO$_4$) and concentrated. Chromatography of the residue on silica gel with 5% MeOH/0.5% NH$_4$OH/CH$_2$Cl$_2$ gave the product which is crystallized from CH$_2$Cl$_2$/heptane to give the titled product 7.

MS (FAB) m/z 586 (M+H$^+$); HRMS (FAB) calcd for C$_{29}$H$_{37}$FN$_5$O$_5$S (M+H$^+$) 586.2499, found 586.2485. Anal. Calcd for C$_{29}$H$_{36}$FN$_5$O$_5$S: C, 59.47; H, 6.20; N, 11.96. Found: C, 59.04; H, 6.25; N, 11.83.

EXAMPLE 2

(S)-N-[[3-[3-Fluoro-4-[4-[(hydroxy acetyl)-1-piperazinyl]phenyl]-2-oxo-5-oxazolidinyl]methyl] propanethioamide 3-[(dimethylamino)methyl] benzoic acid ester (11)

Step 1:

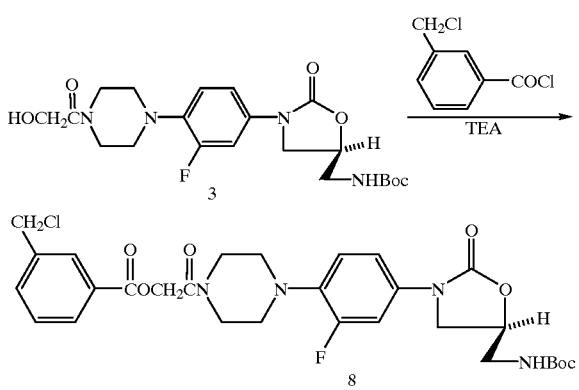

A stirred solution of 3 (Example 1, Step 2) (1.80 g, 3.99 mmol) and triethylamine (0.83 ml, 5.99 mmol) in CH$_2$Cl$_2$ (24 ml) is treated, dropwise with a solution of 3-(chloromethyl)benzoyl chloride (980 mg, 5.18 mmol) in CH$_2$Cl$_2$ (10 ml) and kept at ambient temperature (24° C.) for 18 hours and at reflux for 5 hours. Additional 3-(chloromethyl)benzoyl chloride (150 μl) and triethylamine (166 μl) are added and the mixture is refluxed for 18 hours, mixed with saturated aqueous NaHCO$_3$ and extracted with CH$_2$Cl$_2$. The extract is dried (MgSO$_4$) and concentrated. Chromatography of the residue on silica gel with 2.5% MeOH—CH$_2$Cl$_2$ gave 1.68 g of 8.

Step 2:

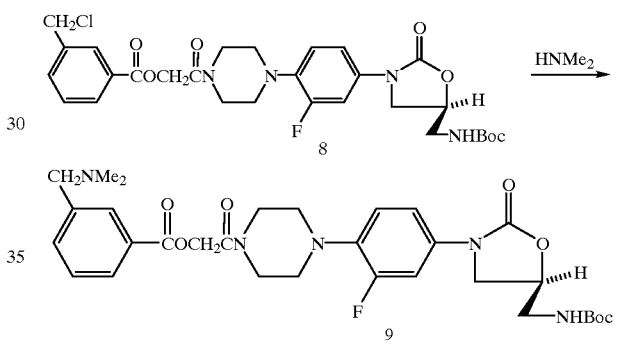

A stirred mixture of 8 (725 mg, 1.20 mmol), sodium iodide (12 mg), 2 M dimethylamine in MeOH (2.3 ml, 4.56 mmol) and acetone (16 ml) is kept at ambient temperature (24° C.) for 4 days, mixed with water and extracted with CH$_2$Cl$_2$. The extract is dried (MgSO$_4$) and concentrated. Chromatography of the residue on silica gel with mixtures of MeOH/CH$_2$Cl$_2$ containing 2.5–5% MeOH gave 632 mg of 9.

Step 3:

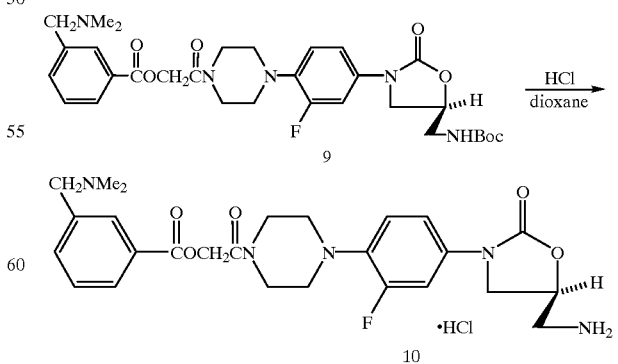

Compound 9 (570 mg, 0.929 mmol) is cooled in an ice bath and treated with 4N HCl in dioxane (10 ml). The mixture is stirred in the ice bath for 2 hours and at ambient temperature (24° C.) for 1.5 hours and concentrated. The residue is mixed with three 40 ml portions of CH$_2$Cl with concentration after and each addition to give 10.

Step 4:

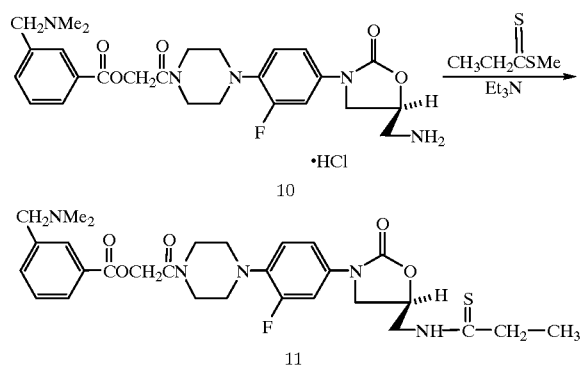

A stirred mixture of 10 (490 mg, 0.891 mmol), triethylamine (0.99 ml, 7.13 mmol) and methyl dithiopropionate (429 mg, 3.56 mmol) in CH$_2$Cl$_2$ (8.5 ml)/THF (8.5 ml) is kept at ambient temperature (24° C.) for 18 hours and concentrated. Chromatography of the residue on silica gel with 5% MeOH/CH$_2$Cl$_2$ gave a mixture of 11 and its hydrochloride salt. This is mixed with saturated aqueous NaHCO$_3$ and extracted with EtOAc. The extract is washed with dilute NaCl, dried (MgSO$_4$) and concentrated. Crystallization of the residue from EtOAc-heptane gave 329 mg of the titled product 11.

Anal. Calcd for C$_{29}$H$_{36}$FN$_5$O$_5$S: C, 59.47; H, 6.20; N, 11.96. Found: C, 59.16; H, 6.30; N, 11.81.

EXAMPLE 3

(S)-N-[[3-[3-Fluoro-4-[4-[(hydroxyacetyl)-1-piperazinyl]phenyl]-2-oxa-5-oxazolidinyl]methyl] propanethioamide 3-(morpholinomethyl)benzoic acid ester (12)

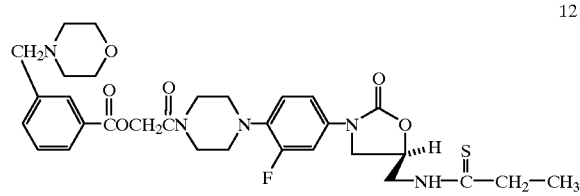

This compound is prepared as described for 11 in Example 2 by substituting morpholine for dimethylamine in Step 2 and refluxing the mixture for 4 days. The titled compound 12 is recrystallized from MeOH and had: MS (EI) m/z 627 (M+).

Anal. Calcd for C$_{31}$H$_{38}$FN$_5$O$_6$S: C, 59.31; H, 6.10; N, 1 1.16. Found: C, 59.32; H, 6.18; N, 11.12.

EXAMPLE 4

(S)-N-[[3-[3-Fluoro-4-[4-(hydroxyacetyl)-1-piperazinyl]phenyl]-2-oxo-5-oxazolidinyl]methyl] propanethioamide 3-[(4-methyl-1-piperazinyl) methyl]benzoic acid ester (13)

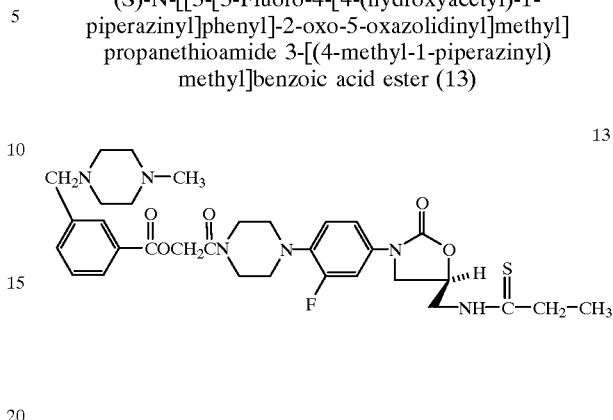

This compound is prepared as described for 11 in Example 2 by substituting 4-methylpiperazine for dimethylamine and CH$_2$Cl$_2$ for acetone in Step 2 and refluxing the mixture for 18 hours to give the titled product (13).

MS (EI) m/z 640 (M$^+$); HRMS (FAB) calcd for C$_{32}$H$_{42}$FN$_6$O$_5$S (M+H$^+$) 641.2921, found: 641.2915.

EXAMPLE 5

(s)-N-[[3-[3-Fluoro-4-[4-(hydroxyacetyl)-1-piperazinyl]phenyl]-2-oxo-5-oxazolidinyl]methyl] propanethioamide 3-[(diethylamino)methyl]benzoic acid ester (14)

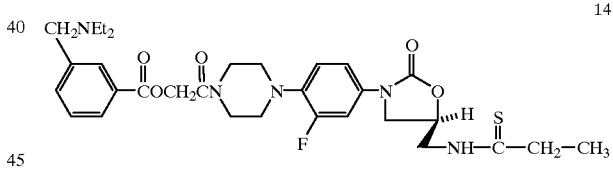

This compound is prepared as described for 11 in Example 2 by substituting diethylamine for dimethylamine in Step 2 and refluxing the mixture for 18 hours. The titled product (14) is crystallized from acetone-heptane.

MS (EI) m/z 613 (M$^+$). Anal. Calcd for C$_{31}$H$_{40}$FN$_5$O$_5$S: C, 60.67; H, 6.57; N, 5 11.41. Found: C, 60.55; H, 6.62; N, 11.39.

EXAMPLE 6

(S)-N-[[3-[3-Fluoro-4-[4-(hydroxyacetyl)-1-piperazinyl]phenyl]-2-oxo-5-oxazolidinyl]methyl] propanethioamide 4-[(diethylamino)methyl]benzoic acid ester (15)

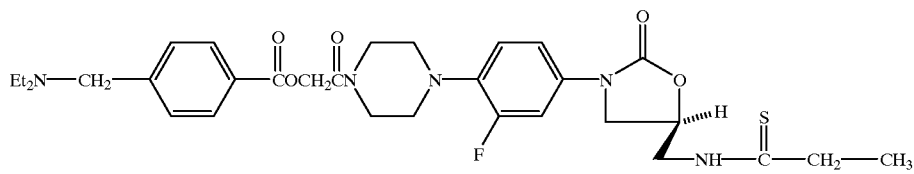

15

Compound 15 is prepared as described for compound 7 in Example 1 by substituting diethylamine for dimethylamine in Step 4 and allowing the reaction to proceed for 2 days at ambient temperature and at reflux for 5 hours. The titled product (15) is crystallized from EtOAc-heptane.

MS (EI) n/z 613 (M$^+$). Anal. Calcd for $C_{31}H_{40}FN_5O_5S$: C, 60.67; H, 6.57; N, 11.41. Found: C, 60.61; H, 6.67; N, 11.32.

EXAMPLE 7

(S)-N-[[3-[3-Fluoro-4-[4-(hydroxyacetyl)-1-piperazinyl]phenyl]-2-oxo-5-oxazolidinyl]methyl] propanethioamide 4-(morpholinomethyl)benzoic acid ester (16)

This compound is prepared as described for compound 7 in Example 1 by substituting morpholine for dimethylamine in Step 4 and refluxing the mixture for 24 hours. The titled product 16 is recrystallized from acetone—$CH_2Cl_2$.

MS (EI) m/z 627 (M$^+$). Anal. Calcd for $C_{31}H_{38}FN_5O_6S$: C, 59.31; H, 6.10; N, 11.16. Found: C,59.17;H,6.21; N, 11.05.

EXAMPLE 8

(S)-N-[[3-[3-Fluoro-4-[4-(hydroxyacetyl)-1-piperazinyl]phenyl]-2-oxo-5-oxazolidinyl]methyl] propanethioamide 4-[(4-methyl-1-piperazinyl) methyl]benzoic acid ester (17)

This compound is prepared as described for compound 7 in Example 1 by substituting 1-methylpiperazine for dimethylamine and $CH_2Cl_2$ for acetone in Step 4 and refluxing the mixture for 24 hours. In Step 6 of this synthesis the product is mixed with saturated aqueous $NaHCO_3$ and extracted with EtOAc to give the pure free base 17, which is recrystallized from acetone-heptane.

MS (EI) m/z 640 (M$^+$); HRMS (FAB) calcd for $C_{32}H_{42}FN_6O_5S$ (M+H+) 641.2921, found: 641.2916. Anal. Calcd for $C_{32}H_{41}FN_6O_5S$: C, 59.98, H, 6.45; N, 13.11. Found: C, 59.70; H, 6.53; N, 13.05.

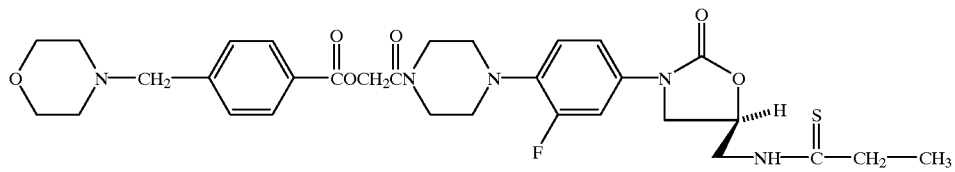

16

EXAMPLE 9

(S)-N-[[3-[3-Fluoro-4-[4-(hydroxyacetyl)-1-piperazinyl]phenyl]-2-oxo-5-oxazolidinyl]methyl] cyclopropanecarbothioamide 4-[(dimethylamino) methyl]benzoic acid ester (18)

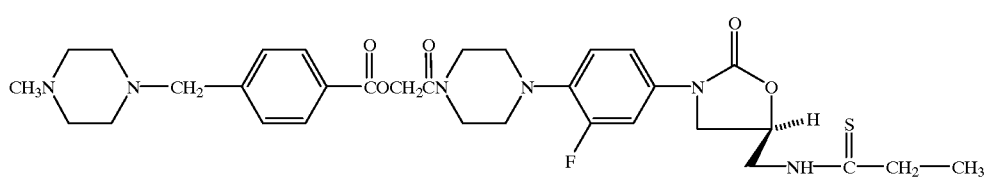

17

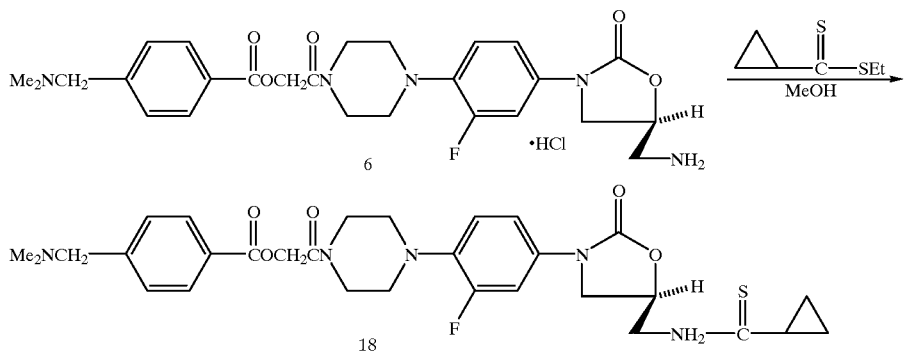

A stirred mixture of 6 (Example 1, Step 5) (792 mg, 1.44 mmol), triethylamine (1.6 ml, 11.5 mmol), ethyl dithiocyclopropanecarboxylate (842 mg, 5.76 mmol) and MeOH (20 ml) is kept at ambient temperature (24° C.) for 2 hours and concentrated. The residue is triturated with EtOAc (15 ml) for 18 hours and the resulting solid is chromatographed on silica gel with 4% MeOH/CH$_2$Cl$_2$. The product is crystallized from EtOAc-heptane to give 388 mg of the title compound 18.

MS (EI) m/z 597 (M$^+$); HRMS (FAB) calcd for C$_{30}$H$_{37}$FN$_5$O$_5$S (M+H$^+$) 598.2499, found: 598.2510. Anal. Calcd for C$_{30}$H$_{36}$FN$_5$O$_5$S: C, 60.28; H, 6.07; N, 11.72. Found: C, 60.06; H, 6.14; N, 11.62.

-continued

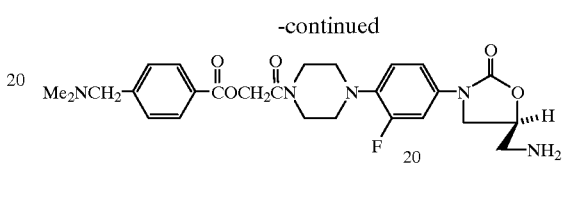

The hydrochloric acid salt (6) prepared from 5 (762 mg, 1.24 mmol) as in Example 1, Step 5 is neutralized with aqueous NaHCO$_3$ and extracted with CH$_2$Cl$_2$. The extract is dried (MgSO$_4$) and concentrated to give 658 mg of 20.

Step 2:

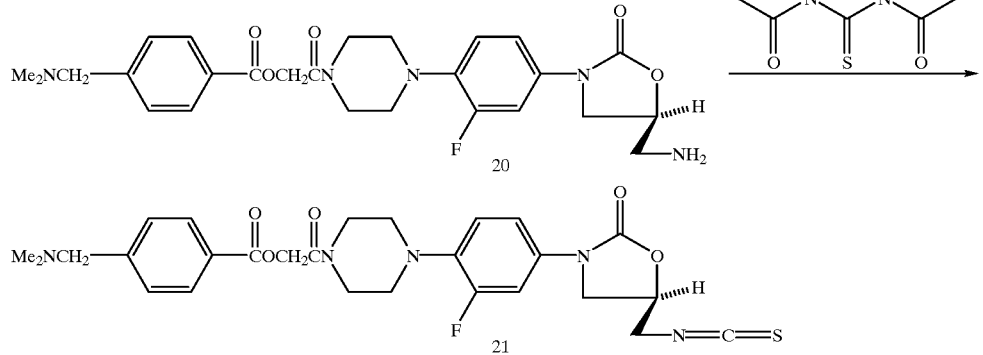

Example 10

(S)-N-[[3-[3-Fluoro-4-[4-(hydroxyacetyl)-1-piperazinyl]phenyl]-2-oxo-5-oxazolidinyl]methyl] thiourea 4-[(simethylamino)methyl]benzoic acid ester (19)

Step 1:

A stirred, ice cold solution of 20 (594 mg, 1.16 mmol) in CH$_2$Cl$_2$ (75 ml) is treated with 1,1'-thiocarbonyldi-2(1H)-pyridone (323 mg, 1.39 mmol), kept at ambient temperature (24° C.) for 18 hours and concentrated. Chromatography of the residue on silica gel with 2.5% MeOH/CH$_2$Cl$_2$ gave a product mixture that is mixed with water and extracted with CH$_2$Cl$_2$. The extract is washed with water, dried (MgSO$_4$) and concentrated to give 483 mg of 21.

Step 3:

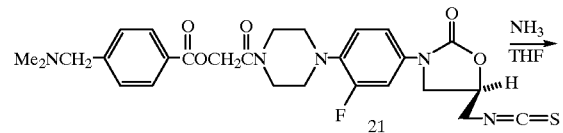

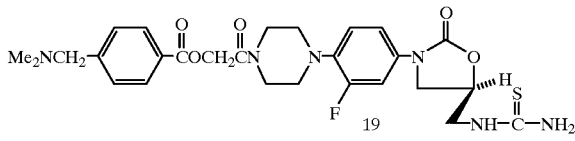

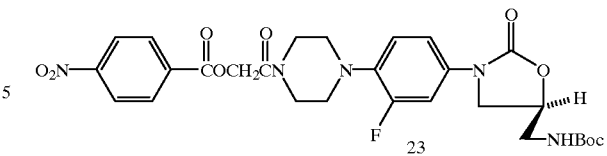

Excess anhydrous ammonia is bubbled into an ice cold solution of 21 (483 mg, 0.869 mmol) in THF (25 ml) and the mixture is stirred for 20 minutes and concentrated. Chromatography of the residue on silica gel with 10% MeOH/CH$_2$Cl$_2$ gave the title compound 19 which is recrystallized from acetonitrile.

MS (EI) m/z 572 (M$^+$). Anal. Calcd for C$_{27}$H$_{33}$FN$_6$O$_5$S: C, 56.63; H, 5.81; N, 14.68. Found: C, 56.41; H, 5.89; N, 14.56.

EXAMPLE 11

(S)-N-[[3-[3-Fluoro-4-[4-(hydroxyacetyl)-1-piperazinyl]phenyl]-2-oxo-5-oxazolidinyl]methyl] propanethioamide 4-(glycylamino)benzoic acid ester (22)

Step 1:

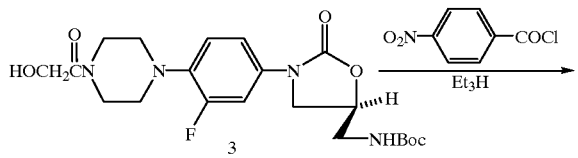

A stirred mixture of 3 (Example 1, Step 2) (1.098 g, 2.43 mmol) and triethylamine (0.70 ml) in CH$_2$Cl$_2$ (20 ml), under nitrogen is treated with 4-nitrobenzoyl chloride (0.553 g, 2.98 mmol) and kept at ambient temperature (24° C.) for 3 hours. It is then treated with 1N HCl (10 ml) and extracted with CH$_2$Cl$_2$. The extract is dried (Na$_2$SO$_4$) and concentrated. Chromatography of the residue on silica gel with 2% MeOH/CH$_2$Cl$_2$ gave 1.24 g of 23.

Step 2:

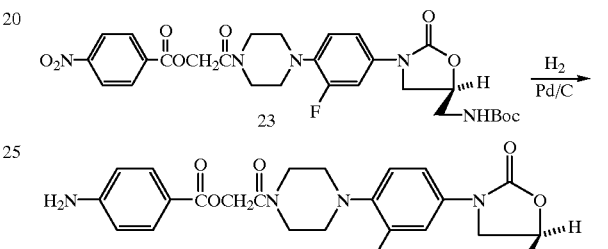

A mixture of 23 (1.24 g, 2.06 mmol), 10% palladium-on-carbon catalyst (0.51 g), MeOH (75 ml) and CH$_2$Cl$_2$ (75 ml) is hydrogenated at an initial pressure of 20 psi for 1 hour 50 minutes and filtered. Concentration of the filtrate gave 1.08 g of 24.

Step 3:

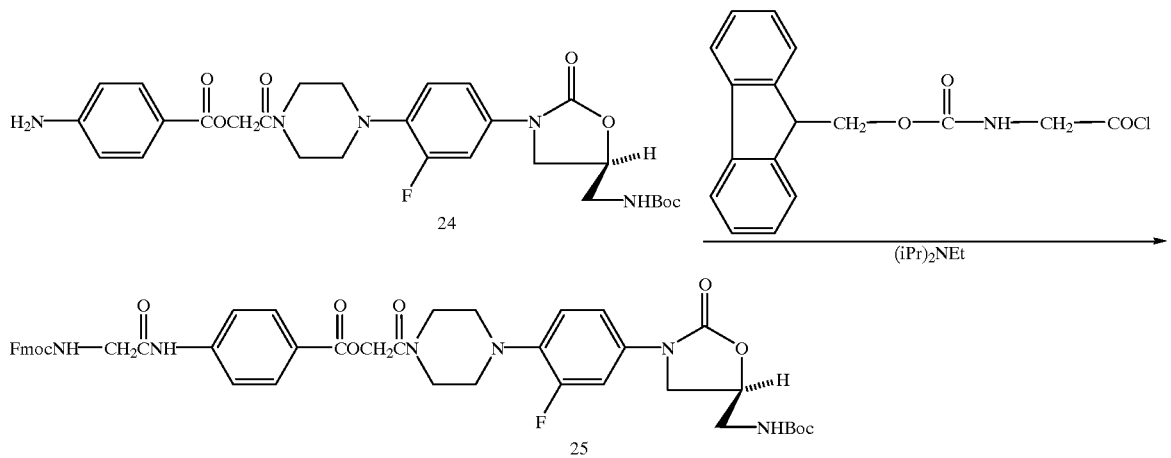

An ice cold, stirred mixture of 24 (0.56 g, 0.98 mmol) and diisopropylethylamine (0.17 ml, 0.96 mmol) in THF (20 ml) under nitrogen is treated portionwise during 80 seconds with N-Fmoc-glycyl chloride (0.336 g, 1.06 mmol) and kept in the ice bath for 1 hour. Additional diisopropylethylamine (9 µl) and N-Fmoc-glycyl chloride (0.04 g) are added and the reaction is continued for 65 minutes. The mixture is concentrated in vacuo and the residue is chromatographed on silica gel with 3% MeOH/CH$_2$Cl$_2$ to give 0.80 g of 25.

Step 4:

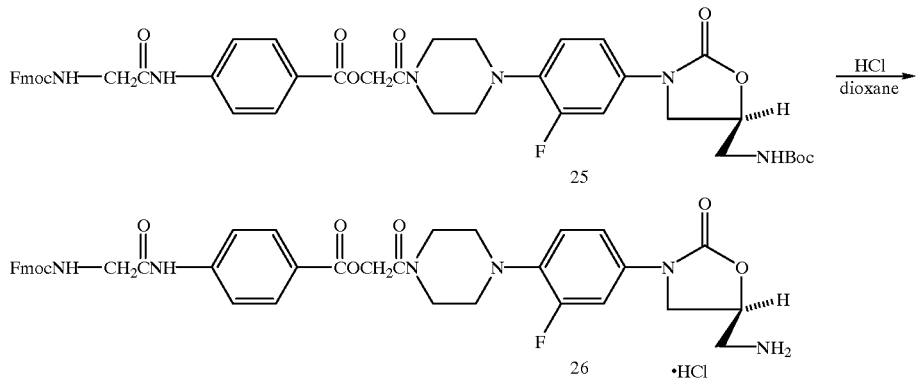

An ice cold solution of 25 (0.23 g, 0.27 mmol) in dioxane (6 ml), under nitrogen, is treated, dropwise with cold 4N HCl in dioxane (3 ml), kept in the ice bath for 100 minutes and at ambient temperature for 2 hours and concentrated in vacuo to give 0.31 g of 26.

Step 5:

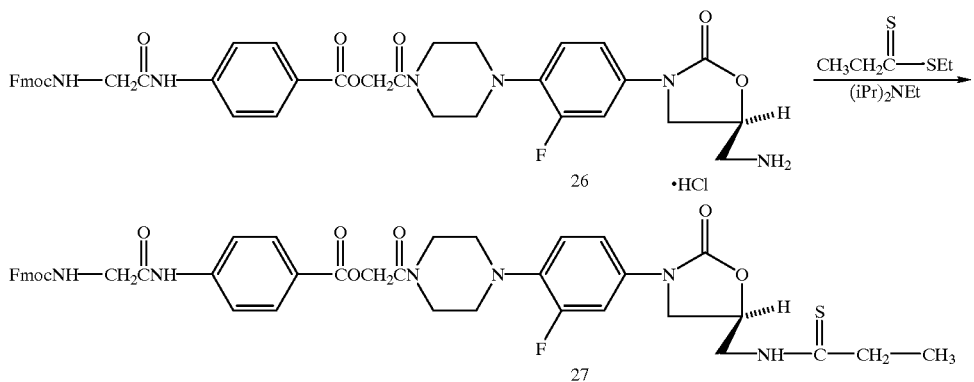

A stirred mixture of 26 (0.20 g), diisopropylethylamine (0.26 ml), THF (6 ml) and $CH_2Cl_2$ (25 ml) is treated with ethyl dithiopropionate (0.10 ml) and kept at ambient temperature (24° C.) for 26 hours. Methanol (5 ml) is added to the mixture which is kept at ambient temperature for 48 hours and at 45–50° C. for 4 hours. It is concentrated and the residue is chromatographed over silica gel with 2.5% MeOH/$CH_2Cl_2$ to give 0.09 g of 27.

Step 6:

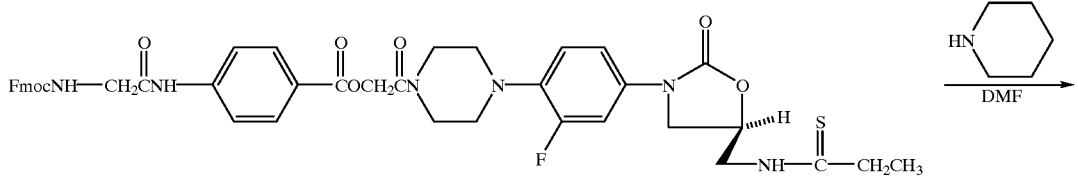

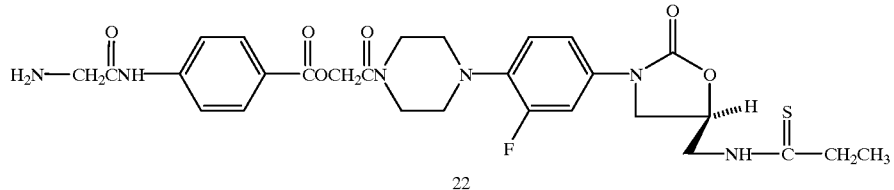

A stirred solution of 27 (0.09 g) in DMF (1 ml), under nitrogen, is treated with piperidine (0.027 ml), kept at ambient temperature for 15 min and concentrated in vacuo. Chromatography of the residue on silica gel with 0.4% $NH_4OH$/4% MeOH/$CH_2Cl_2$ gave the title compound 22. HRMS (FAB) calcd for $C_{28}H_{34}FN_6O_6S$ (M+H$^+$) 601.2244, found 601.2251.

EXAMPLE 12

(S)-N-[[3-[3-Fluoro-4-[4-(hydroxyacetyl)-1-piperazinyl]phenyl]-2-oxo-5-oxazolidinyl]methyl] cyclopropanecarbothioamide 4-(glycylamino) benzoic acid ester (28)

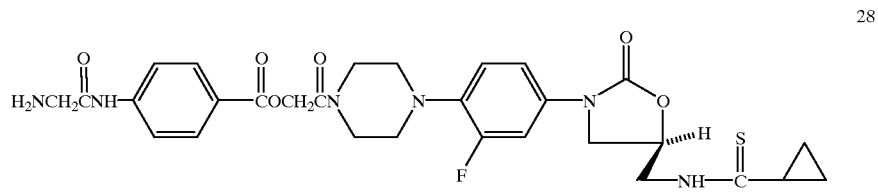

The title compound 28 is prepared as described for compound 22 in Example 11 by substituting ethyl dithiocyclopropanecarboxylate for ethyl dithiopropionate in Step 5 which is carried out in MeOH at 45° C.

HRMS (FAB) calcd for $C_{29}H_{34}FN_6O_6S$ (M+H$^+$) 613.2244, found 613.2233.

EXAMPLE 13

(S)-N-[[3-[3-Fluoro-4-[4-(hydroxyacetyl)-1-piperazinyl]phenyl]-2-oxo-5-oxazolidinyl]methyl] propanethioamide 4-(L-alanylamino)benzoic acid ester (29)

Step 1:

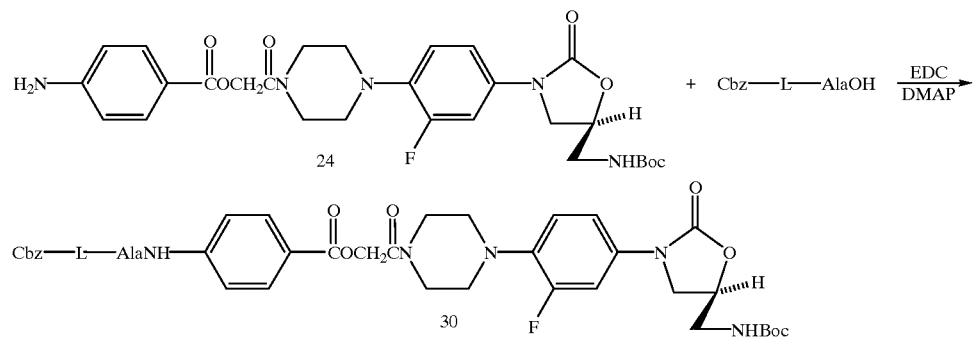

A stirred mixture of carbobenzyloxy-L-alanine (0.48 g, 0.0022 mol) and 1-(3-dimethylaminopropyl)-3-ethylcarbodiimide hydrochloride (EDC, 0.43 g, 0.0023 mol) in pyridine (15 ml) was kept, under nitrogen, for 5 minutes and treated with 4-(dimethylamino)pyridine (15 mg) and 24 (Example 11, Step 2) (1.0 g, 0.0018 mol). The mixture was kept at ambient temperature (24° C.) for 21 hours, treated with additional carbobenzyloxy-L-alanine (0.20 g) and EDC (0.18 g), kept at ambient temperature for 6 hours and at 0° C. for 72 hours and concentrated in vacuo. Chromatography of the residue on silica gel with 2.5% MeOH—CHCl₃ gave 1.1 g of 30: MS (ES) m/z 777 (M+H⁺), 799 (M+Na⁺)

Step 2:

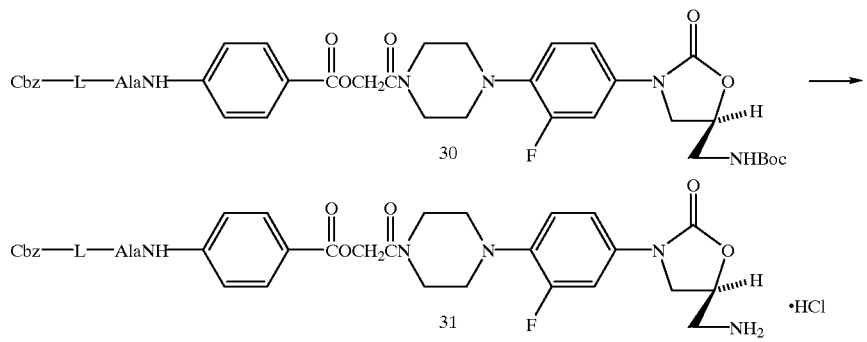

An ice cooled, stirred mixture of 30 (1.1 g) and dioxane (20 ml), under nitrogen, was treated during 3 minutes with ice cold 4N hydrogen chloride in dioxane (10 ml) and kept in the ice bath for 1 hour and at ambient temperature for 2 hours and 20 minutes. Excess hydrogen chloride was removed under a stream of nitrogen and the remaining mixture was concentrated in vacuo to give 1.1 g of 31, a white solid: MS (ES) m/z 677 (M+H⁺).

Step 3:

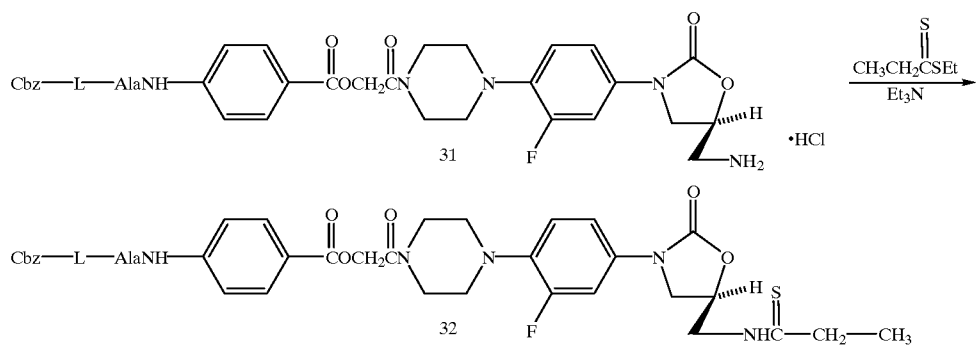

A stirred mixture of 31 (0.5 g) and triethylamine (0.36 ml) in methanol (10 ml) under nitrogen, was treated with ethyl dithiopropionate (0.10 ml) and kept at ambient temperature for 1 hour 45 minutes. The solid was collected by filtration and washed with cold MeOH to give 0.26 g of 32, a white solid: MS (ES) m/z 749 (M+H⁺).

Step 4:

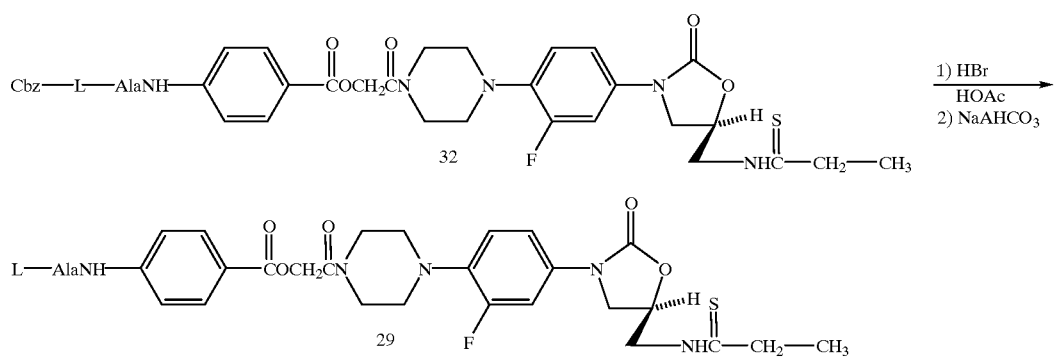

Compound 32 (0.13 g) was treated with 30% hydrogen bromide in acetic acid (3.8 ml) stirred at ambient temperature for 30 minutes and mixed with $Et_2O$ (25 ml). The supernatant liquid was decanted and the residue was washed twice with $Et_2O$ and collected by filtration. A solution of the solid in water was neutralized (pH 9–10) with saturated aqueous $NaHCO_3$ and the resultant solid was collected by filtration and washed with water to give 0.073 g of product. It was combined with the product (0.097 g) from a second identical reaction and chromatographed on silica gel with 4% MeOH—0.2% $NH_4OH$—$CH_2Cl_2$. Crystallization of the resulting product from MeOH gave 0.071 g of 29: mp 220–221° C. HRMS (FAB) calcd for $C_{29}H_{36}FN_6O_6S$ $(M+H^+)$ 615.2401, found 615.2405.

What is claimed is:

1. A compound of formula I:

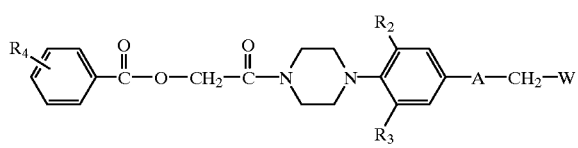

I or a pharmaceutically acceptable salt thereof wherein:

A is a structure i, ii, or iii

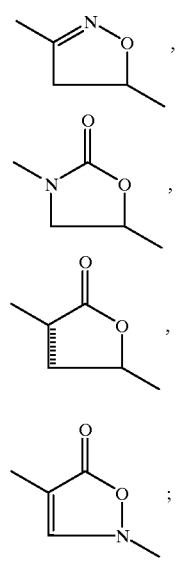

W is a) $NHC(=X)R_1$,
b) —O—het, —S—het, or —NH—het; provided that when A is a structure iv, W is not the section b);

X is O, or S;

$R_1$ is
(a) H,
(b) $NH_2$,
(c) $NHC_{1-4}$alkyl,
(d) $C_{1-4}$alkyl, optionally substituted by one or more F, Cl, or CN,
(e) $C_{2-4}$alkenyl,
(f) $OC_{1-4}$alkyl,
(g) $SC_{1-4}$alkyl, or
(h) $(CH_2)_nC_{3-6}$cycloalkyl;

$R_2$ and $R_3$ are independently H, F, Cl or $C_{1-2}$alkyl;

$R_4$ is positioned at either C-3 or C-4 and is:

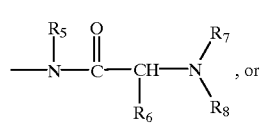

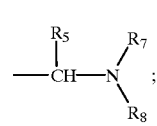

$R_5$ is H, or $CH_3$;

$R_6$ is H, or $C_{1-4}$alkyl, optionally substituted by OH, SH, $SCH_3$, $NH_2$ or $NHC(=NH)NH_2$;

$R_7$ and $R_8$ are independently
(a) H,
(b) $C_{1-4}$alkyl, or
(c) $R_7$ and $R_8$ together with the nitrogen to which they are attached to form a saturated 5-, 6-, or 7-membered heterocyclic ring which may have additional heteroatoms selected from the group consisting of O, $S(O)_n$, or or N—$R_5$; het is a C-linked five- (5) or six- (6) membered saturated or unsaturated heterocyclic ring having 1, 2, or 3 heteroatoms selected from the group consisting of oxygen, sulfur, and nitrogen, which is optionally fused to a benzene ring; at each occurrence, wherein het is optionally substituted with one or more halo, OH, $CF_3$, $OC_{1-6}$alkyl, CN, $C_{1-6}$ alkyl, $S(=O)_iR^9$, $C(=X)R^{10}$, $OC(=O)R^{10}$, $NHC(=O)R^{10}$, or $NR^{10}R^{10}$, oxo, or oxime; wherein $R^9$ is $C_{1-6}$alkyl, aryl, or $NR^7R^8$; $R^{10}$ is H, $C_{1-6}$alkyl, aryl, or $NR^7R^8$;

n is 0, 1, or 2; and with the proviso that when X is O, $R_4$ is not the subsection (a).

2. A compound of claim 1 which is a compound of formula IA

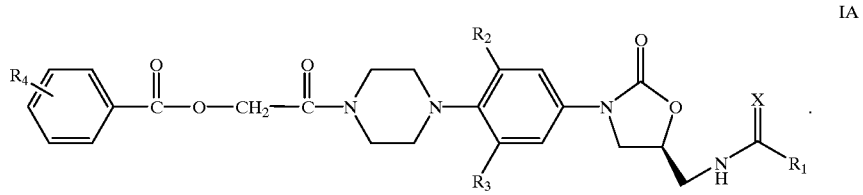

IA

3. A compound of claim 2 wherein $R_1$ is $C_{1-4}$alkyl.
4. A compound of claim 2 wherein $R_1$ is ethyl.
5. A compound of claim 2 wherein $R_1$ is $NH_2$.

6. A compound of claim 2 wherein $R_1$ is $C_{3-6}$cycloalkyl.

7. A compound of claim 1 wherein X is sulfur atom.

8. A compound of claim 1 wherein X oxygen atom.

9. A compound of claim 1 wherein $R_2$ and $R_3$ are independently H or F.

10. A compound of formula I according to claim 1 wherein at least one of said $R_2$ and $R_3$ is H, the other one is F.

11. A compound of claim 1 wherein $R_4$ is —$CH_2N(CH_3)_2$.

12. A compound of claim 1 wherein $R_4$ is 4-morpholinylmethyl.

13. A compound of claim 1 wherein $R_4$ is 4-methyl-1-piperazinylmethyl.

14. A compound of claim 1 wherein $R_4$ is

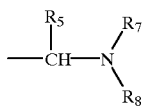

wherein $R_5$, $R_7$ and $R_8$ are the same as defined in claim 1.

15. A method for treating microbial infections comprising: administering to a mammal in need thereof an effective amount of a compound of formula I as shown in claim 1.

16. The method of claim 15 wherein said compound of formula I is administered orally, parenterally, transdermally, or topically in a pharmaceutical composition.

17. The method of claim 15 wherein said compound is administered in an amount of from about 0.1 to about 100 mg/kg of body weight/day.

18. The method of claim 15 wherein said compound is administered in an amount of from about 1 to about 50 mg/kg of body weight/day.

19. A method for treating microbial infections of claim 15 wherein the infection is skin infection.

20. A method for treating microbial infections of claim 15 wherein the infection is eye infection.

21. A pharmaceutical composition comprising a compound of claim 1 and a pharmaceutically acceptable carrier.

22. A compound of claim 1 which is selected from the group consisting of
(1) (S)-N-[[3-[3-fluoro-4-[4-(hydroxyacetyl)-1-piperazinyl]phenyl]-2-oxo-5-oxazolidinyl]methyl]propanethioamide 4-[(dimethylamino)methyl]benzoic acid ester,
(2) (S)-N-[[3-[3-fluoro-4-[4-[(hydroxy acetyl)-1-piperazinyl]phenyl]-2-oxo-5-oxazolidinyl]methyl] propanethioamide 3-[(dimethylamino)methyl]benzoic acid ester,
(3) (S)-N-[[3-[3-fluoro-4-[4-[(hydroxyacetyl)-1-piperazinyl]phenyl]-2-oxo-5-oxazolidinyl]methyl] propanethioamide 3-(morpholinomethyl)benzoic acid ester,
(4) (S)-N-[[3-[3-fluoro-4-[4-(hydroxyacetyl)-1-piperazinyl]phenyl]-2-oxo-5-oxazolidinyl]methyl]propanethioamide 3-[(4-methyl-1-piperazinyl)methyl]benzoic acid ester,
(5) (S)-N-[[3-[3-fluoro-4-[4-(hydroxyacetyl)-1-piperazinyl]phenyl]-2-oxo-5-oxazolidinyl]methyl]propanethioamide 3-[(diethylamino)methyl]benzoic acid ester,
(6) (S)-N-[[3-[3-fluoro-4-[4-(hydroxyacetyl)-1-piperazinyl]phenyl]-2-oxo-5-oxazolidinyl]methyl]propanethioamide 4-[(diethylamino)methyl]benzoic acid ester,
(7) (S)-N-[[3-[3-fluoro-4-[4-(hydroxyacetyl)-1-piperazinyl]phenyl]-2-oxo-5-oxazolidinyl]methyl]propanethioamide 4-(morpholinomethyl)benzoic acid ester,
(8) (S)-N-[[3-[3-fluoro-4-[4-(hydroxyacetyl)-1-piperazinyl]phenyl]-2-oxo-5-oxazolidinyl]methyl]propanethioamide 4-[(4-methyl-1-piperazinyl)methyl]benzoic acid ester,
(9) (S)-N-[[3-[3-fluoro-4-[4-(hydroxyacetyl)-1-piperazinyl]phenyl]-2-oxo-5-oxazolidinyl]methyl] cyclopropanecarbothioamide 4-[(dimethylamino)methyl]benzoic acid ester,
(10) (S)-N-[[3-[3-fluoro-4-[4-(hydroxyacetyl)-1-piperazinyl]phenyl]-2-oxo-5-oxazolidinyl]methyl] thiourea 4-[(dimethylamino)methyl]benzoic acid ester,
(11) (S)-N-[[3-[3-fluoro-4-[4-(hydroxyacetyl)-1-piperazinyl]phenyl]-2-oxo-5-oxazolidinyl]methyl] propanethioamide 4-(glycylamino)benzoic acid ester,
(12) (S)-N-[[3-[3-fluoro-4-[4-(hydroxyacetyl)-1-piperazinyl]phenyl]-2-oxo-5-oxazolidinyl]methyl] cyclopropanecarbothioamide 4-(glycylamino)benzoic acid ester, or
(13) (S)-N-[[3-[3-Fluoro-4-[4-(hydroxyacetyl)-1-piperazinyl]phenyl]-2-oxo-5-oxazolidinyl]methyl] propanethioamide 4-(L-alanylamino)benzoic acid ester.

23. A compound of claim 1 which is selected from the group consisting of
(1) (S)-N-[[3-[3-fluoro-4-[4-(hydroxyacetyl)-1-piperazinyl]phenyl]-2-oxo-5-oxazolidinyl]methyl]propanethioamide 4-[(dimethylamino)methyl]benzoic acid ester,
(2) (S)-N-[[3-[3-fluoro-4-[4-(hydroxyacetyl)-1-piperazinyl]phenyl]-2-oxo-5-oxazolidinyl]methyl]propanethioamide 4-(morpholinomethyl)benzoic acid ester, or
(3) (S)-N-[[3-[3-fluoro-4-[4-(hydroxyacetyl)-1-piperazinyl]phenyl]-2-oxo-5-oxazolidinyl]methyl]propanethioamide 4-[(4-methyl-1-piperazinyl)methyl]benzoic acid ester.

24. A compound of claim 1 wherein structure i, or iii is

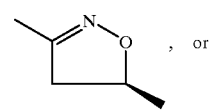, or

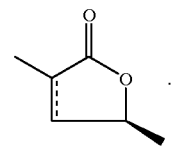

* * * * *